(12) United States Patent
     Koseoglu (10) Patent No.: US 9,423,391 B2
(45) Date of Patent: *Aug. 23, 2016

(54) RELATIVE VALUATION METHOD FOR NAPHTHA STREAMS

(71) Applicant: SAUDI ARABIAN OIL COMPANY, Dhahran (SA)

(72) Inventor: Omer Refa Koseoglu, Dhahran (SA)

(73) Assignee: Saudi Arabain Oil Company, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 14/589,257

(22) Filed: Jan. 5, 2015

(65) Prior Publication Data

US 2015/0112610 A1     Apr. 23, 2015

Related U.S. Application Data

(63) Continuation-in-part of application No. 13/275,001, filed on Oct. 17, 2011, now Pat. No. 8,930,149.

(60) Provisional application No. 61/394,131, filed on Oct. 18, 2010.

(51) Int. Cl.
    *G01N 33/28*     (2006.01)
    *G01N 30/02*     (2006.01)
    (Continued)

(52) U.S. Cl.
    CPC ............ *G01N 33/2829* (2013.01); *C10G 35/00* (2013.01); *C10G 35/24* (2013.01); *G01N 30/02* (2013.01); *G06F 19/704* (2013.01); *C10G 2300/1044* (2013.01); *C10G 2300/305* (2013.01); *C10G 2400/02* (2013.01); *G01N 2030/025* (2013.01)

(58) Field of Classification Search
    CPC .................................................. G01N 33/2829
    USPC ........................................................... 702/24
    See application file for complete search history.

(56) References Cited

U.S. PATENT DOCUMENTS 4,251,870 A     2/1981   Jaffe
5,223,714 A     6/1993   Maggard
(Continued)

FOREIGN PATENT DOCUMENTS

WO          2006030218 A1      3/2006

OTHER PUBLICATIONS

Birch, Oil & Gas Journal, Jan. 14, 2002, pp. 54-59 (printed Jul. 9, 2014 from http://www.ogj.com/articles/print/volume-100/issue-2/processing/achieving-maximum-crude-oil-value-depends-on-accurate-evaluation.html).

(Continued)

*Primary Examiner* — Bryan Bui
(74) *Attorney, Agent, or Firm* — Abelman, Frayne & Schwab (57) ABSTRACT

A system and a method for determining the relative value of a naphtha product includes reforming the naphtha into fractions at a predetermined constant research octane number (RON), conducting PIONA analysis on the reformate, after which modules or steps are performed to assign the feed quality, assign the total liquid yields, assign raw product yields, normalize the assigned raw product yields, assign a value to one or more fractions, and calculate a total value of the naphtha stream. The method is repeated on samples of different crude oils in order to provide relative values at the predetermined RON for comparison purposes.

12 Claims, 3 Drawing Sheets

(51) Int. Cl.
  *C10G 35/00* (2006.01)
  *C10G 35/24* (2006.01)
  *G06F 19/00* (2011.01)

(56) References Cited

U.S. PATENT DOCUMENTS

| | | | |
|---|---|---|---|
| 5,452,232 | A | 9/1995 | Espinosa et al. |
| 5,490,085 | A | 2/1996 | Lambert et al. |
| 5,572,030 | A | 11/1996 | Ranson et al. |
| 5,600,134 | A | 2/1997 | Ashe et al. |
| 5,699,269 | A | 12/1997 | Ashe et al. |
| 5,712,797 | A * | 1/1998 | Descales .............. G01N 21/359 702/30 |
| 6,258,987 | B1 | 7/2001 | Schmidt et al. |
| 6,602,403 | B1 | 8/2003 | Steffens et al. |
| 8,930,149 | B1 * | 1/2015 | Koseoglu ................ G06F 19/00 702/25 |
| 2002/0052769 | A1 | 5/2002 | Navani et al. |
| 2007/0050154 | A1 | 3/2007 | Albahri |
| 2008/0040051 | A1 | 2/2008 | Franklin et al. |
| 2015/0112611 | A1 * | 4/2015 | Koseoglu ........... G01N 33/2823 702/25 |

OTHER PUBLICATIONS

Pavlovic, Oil & Gas Journal, Nov. 22, 1999, pp. 51-56 (printed Jul. 9, 2014 from http://www.ogj.com/articles/print/volume-97/issue-47/in-this-issue/refining/gravity-and-sulfur-based-crude-valuations-more-accurate-than-believed.html).

* cited by examiner

RELATIVE VALUATION METHOD FOR NAPHTHA STREAMS

RELATED APPLICATIONS

The subject application is a continuation-in-part of U.S. patent application Ser. No. 13/275,001 filed Oct. 17, 2011, which claims priority to U.S. Provisional Patent Application No. 61/394,131 filed Oct. 18, 2010, which are both incorporated by reference in their entireties.

FIELD OF THE INVENTION

This invention relates to a method and process for the evaluation of samples of crude oil and its fractions by PIONA gas chromatography analysis.

BACKGROUND OF THE INVENTION

There are more than 200 crude oils produced and traded worldwide. Crude oils are very complex mixtures of many thousands of different hydrocarbons. Depending on the source, the oils contain various proportions of straight and branched-chain paraffins, cycloparaffins, and naphthenic, aromatic and polynuclear aromatic hydrocarbons. The nature of the crude oil governs, to a certain extent, the nature of the products that can be manufactured from it and their suitability for specific applications.

Worldwide supply and demand, regional refining capacities and configurations, and crude composition are the key factors that determine the value of crude oil. The first factor is purely market-dependent and cannot be predicted from the crude oil quality. Accordingly, the crude oil value is determined by the regional crude market and differentials such as freight, quality adjustments, refining cost and competitive pricing.

In a typical petroleum refinery, crude oil is first distilled under atmospheric pressure. Gases will rise to the top of the distillation column, followed by lower boiling liquids, including, naphtha, kerosene and diesel oil. Naphtha is not a final product, but is subjected to additional treatment steps, such as hydrotreating and catalytic reforming to produce reformate. The reformate is then sent to a gasoline pool for blending.

An article by Colin Birch, "Achieving Maximum Crude Oil Values Depends on Accurate Evaluation," Oil & Gas Journal, Vol. 100, Issue 2 (Jan. 14, 2002), describes a number of evaluation methods for obtaining an objective calculation of the value of a specific crude oil from a particular source. Summaries of several of these methods follow.

Bulk-Property Method: This method correlates actual crude value with bulk properties. API gravity and sulfur content are widely used for the correlation, and other bulk properties, such as viscosity and pour point, can also be used. This method is relatively simple in terms of the amount of testing required. However, this method may not be reliable when a large range of crudes are being valued. For example, some of the naphthenic crudes may be valued relatively higher, using this method, but this result may not reflect the actual market value for the crude oil.

Refining-Value Method: Crude oils are evaluated and valued using the refinery yields and process operating costs for each crude stream, typically using a linear program (LP) or other model. Refinery models require detailed physical property information and distillation cuts as determined by a detailed crude oil assay. Process yields and operating costs are used with appropriate product values to calculate refining-value differentials between the crude oils. The refining-value method simulates the process used by refiners for selecting crude oils. Detailed crude oil quality information and the need to run a refinery model for a given refinery to generate the yields make this method more complex than the bulk-property method. If input stream quality changes significantly, a new set of yields must be generated. In relatively simple systems involving only a few crudes with reasonably stable quality, the refining-value method normally provides the most accurate value allocation for a refiner.

Distillation-Yield Method: This is a simplified version of the refining-value method, which instead of using a linear program or other model will only use the yield of each fraction. These product yields from distilling each crude are used with product values to calculate the relative value of each crude. In many cases, some physical properties of the distillation cuts are used in the value-adjustment system. The quality information from each crude is relatively simple and includes distillation yields and distillation cut properties. The distillation yield-method is more complex than the bulk-property method, but less complex than the refining-value method. Because it uses product values in the calculation, reliability of crude oil value data is not an issue. The products being valued, however, such as naphtha, are not finished products meeting defined specifications. So there is some uncertainty regarding the value adjustment for key properties of the distillation cuts.

Several properties of naphtha streams can be evaluated, including API gravity, sulfur, nitrogen, carbon and hydrogen contents, and research octane number. Research octane number is the measure of a fuel's ability to prevent detonation in a spark-ignition engine. Measured in a standard single-cylinder, variable-compression-ratio engine by comparison with primary reference fuels, American Standard Testing Material Tests ASTM D-2699 and ASTM D-2700 describe the determination of research and motor octane numbers, respectively. Under mild conditions, the engine measures research octane number (RON), while under sever conditions the engine measures motor octane number (MON). Where the law requires posting of octane numbers on dispensing pumps, the anti-knock index (AKI) is used. This is the arithmetic average of RON and MON, namely, (R+M)/2. It approximates the road octane number, which is a measure of how an "average" car responds to fuel. It is the most critical property for naphtha/gasoline streams.

The RON of a spark-ignition engine fuel is determined using a standard test engine and operating conditions to compare its knock characteristic, defined as knock intensity (KI) with those of primary reference fuel (PRF) blends (containing iso-octane and normal heptane) of known octane number. For example, an 87-octane gasoline has the same octane rating as a mixture of 87% iso-octane and 13% n-heptane. Compression ratio (CR) and fuel-air ratio are adjusted to produce standard KI for the sample fuel, as measured by a specific electronic detonation meter instrument system. A standard KI guide table relates engine CR to octane number level for this specific method. The fuel-air ratio for the sample fuel and each of the primary reference fuel blends is adjusted to maximize KI for each fuel. While gasoline will have an RON of 85 or higher, naphtha will have an RON below 60.

The MON of a spark-ignition engine fuel is determined using a standard test engine and operating conditions to compare its knock characteristic with those of PRF blends of known octane number. CR and fuel-air ratios are adjusted to produce standard KI for the sample fuel, as measured by a specific electronic detonation meter instrument system. A standard KI guide table relates engine CR to octane number level for this specific method. The fuel-air ratio for the sample fuel and each of the PRF blends is adjusted to maximize KI for each fuel.

To determine these properties of gas oil or naphtha fractions conventionally, these fractions have to be distilled from the crude oil and then measured/identified using various analytical methods that are laborious, costly and time-consuming.

Therefore, a need exists for an improved system and method for determining the value of crude oils from different sources that can be objectively applied to compare the naphtha fractions from different sources.

SUMMARY OF THE INVENTION

Systems and methods for assigning a value to a naphtha stream are provided. The stream is reformed to a target research octane number, and plural light component fractions and a reformate fraction are obtained; the reformate fraction is analyzed to obtain data indicative of the content naphthenes and aromatics, and in certain embodiments additionally paraffins and iso-paraffins, and in further embodiments additionally paraffins, iso-paraffins olefins, and iso-olefins. The indicative data is used to assign a feed quality. The assigned feed quality is used to assign a total liquid yield and raw products yields, which are individually assigned values. A total naphtha valuation can thus be assigned based on the indicative data. When the method is applied to naphtha streams derived from crude oils from various sources, the respective assigned values provide an objective basis for relative evaluation of the crude oil.

The system and method of the invention can be utilized to valuate naphtha fractions derived from crude oils, which fractions have nominal boiling points in the range of −11.5 to 235° C., and in certain embodiments from 36-180° C. Naphtha fractions vary in composition and, as a result, octane number, which, as discussed above, is a key indicative property for engine-knocking characteristic. The difference in composition and properties make the evaluation of the naphtha fraction difficult. In a certain embodiments, the comparative evaluation method disclosed herein is practiced on straight run naphtha samples.

In certain embodiments of the method herein, the naphtha fraction is converted to light components and a reformate of a target research octane number in a catalytic reforming process. The reformate is fed into a gas chromatograph to obtain data indicative of the content naphthenes and aromatics, and in certain embodiments additionally paraffins and iso-paraffins, and in further embodiments additionally paraffins, iso-paraffins olefins, and iso-olefins, e.g., known as a PIONA analysis. An algorithm is applied to the total percentages of the naphthenes and aromatics in order to determine a value of the naphtha stream. The value of each of the components is assigned based upon independently determined values at a given time and place that is predetermined by the user.

The methods and systems herein can be applied to samples derived from different crude oils obtained from different reservoirs or regions to provide relative values for the same RON in order to provide refiners with a basis for comparison in the market(s) in which their products are sold. Accordingly, an object of the method and system herein is to facilitate comparison of two or more streams in order to ascertain which stream has a higher value based upon the current value for its constituent fractions. Such data is useful, for instance, to provide the refiner with a basis for deciding which stream should be processed first.

Another object of this invention is to provide a method for evaluation of particular naphtha streams derived from crude oils from various sources to establish an objective basis for economic comparison based on specific value.

In the description herein, the terms "reformer unit", "reformer" and "reforming unit" are used interchangeably, and refer to conventional apparatus used in a catalytic reforming process.

BRIEF DESCRIPTION OF THE DRAWINGS

Further advantages and features of the present invention will become apparent from the following detailed description of the invention when considered with reference to the accompanying drawing, in which.

DETAILED DESCRIPTION OF INVENTION

A system and method is provided for determining and assigning yields and valuation of a hydrocarbon sample. Reformate component yields of a naptha fraction derived in certain embodiments from crude oil samples are assigned as a function of the PIONA analysis data of a crude oil sample. The correlations also provide information about naphtha component and total yields without fractionation/distillation (crude oil assays) and enables producers, refiners, and marketers to benchmark the oil quality and, as a result, valuate the oils without performing the customary extensive and time-consuming crude oil assays.

The systems and methods are applicable for evaluation of naphtha streams derived from crude oils, bitumens, heavy oils, shale oils and from refinery process units including hydrotreating, hydroprocessing, fluid catalytic cracking, coking, and visbreaking or coal liquefaction.

Figure 1:
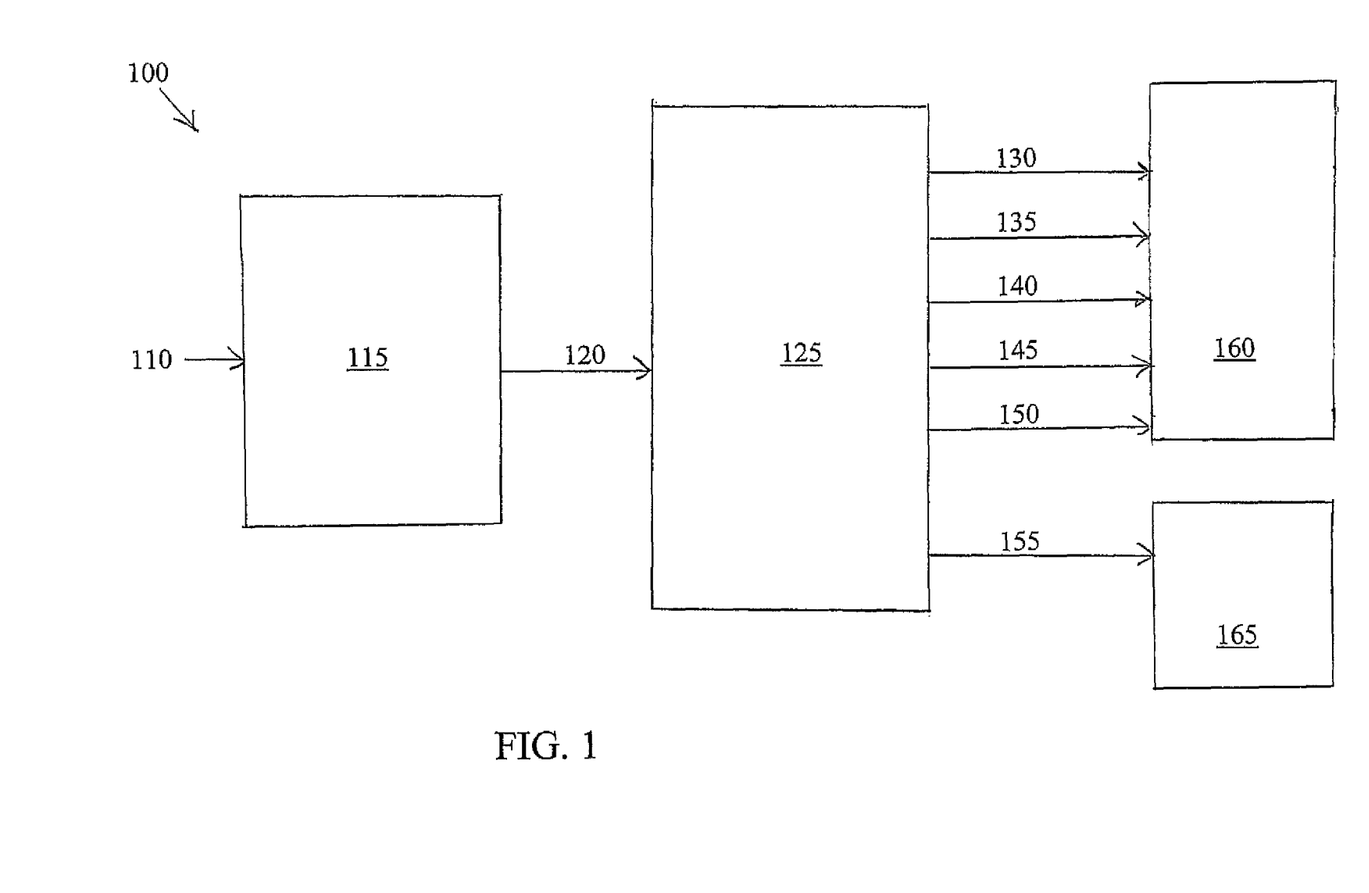
FIG. 1 schematically illustrates the hydrotreating and reformation of naphtha and the chromatograph analysis of the resultant streams.

FIG. 1 shows the hydrotreating and reforming process 100. A naphtha stream 110 to be evaluated is fed into a hydrotreater 115 to produce a hydrotreated naphtha stream 120, which is passed to a reformer 125. Light component streams hydrogen ("H2") 130, methane ("C1") 135, ethane ("C2") 140, propane ("C3") 145, and butane ("C4") 150, and reformate ("C5+") 155, are recovered from reformer 125. Operating conditions are such that the reformate is characterized by a target research octane number. Thus, while the product yield distribution will differ for each naphtha feedstock produced, the quality of gasoline, as measured by the research octane number, will be uniform.

The predetermined research octane number selected can be in the range of from 80 to 100 for products coming from the reforming unit, in certain embodiments in the range of from 95 to 100, and in further embodiments in the range of from 95 to 98, which is the gasoline RON specification. It is to be noted that the yield typically declines with an increase in the target octane number.

In certain embodiments, hydrotreater 115 operates under conditions and in the presence of one or more catalysts effective to produce a hydrotreated naphtha stream 120 having sulfur levels below 0.5 ppmw and nitrogen levels below 0.5 ppmw. The maximum allowable sulfur and nitrogen contaminant content levels should be maintained within the predetermined limits established for efficient use of the reformer unit catalyst. The reformer catalyst is made of noble metals such as platinum and palladium and is very sensitive to impurities like sulfur and nitrogen. The presence of higher levels of sulfur and nitrogen during the operation will poison the catalyst. As is known to those of ordinary skill in the art, the major sources of sulfur are inadequate hydrotreating, hydrotreating stripper upsets and the recombination of hydrogen sulfide and olefins at high temperature and low pressures. The principal sources of nitrogen are inadequate hydrotreating, cracked naphtha in the feedstock, and improper use of inhibitors. Since the reforming unit catalyst can be quite sensitive to impurities, in certain embodiments sulfur and nitrogen levels are reduced in the hydrotreating process to provide a reformer feedstream meeting the requisite specification.

The separated light gases 130, 135, 140, 140, 150 are passed into one or more refinery gas analyzers 160, for instance in certain embodiments gas chromatographs that analyze the gases in accordance with ASTM D1945.

Liquid reformate 155 is fed into PIONA analyzer 165. In certain embodiments PIONA analyzer 165 is a gas chromatograph that analyzes the liquid in accordance with ASTM D6839. In the PIONA analysis, fractions of the reformate are tabulated by carbon number and n-paraffins, i-paraffins, naphthenes and aromatics, showing the percentage volume for each carbon number. In certain embodiments, the reformate is derived from straight-run naphtha from crude oil distillation, as opposed to being derived from intermediate refinery naphtha from cracking reactions, and accordingly no or few olefins are present.

Figure 2:
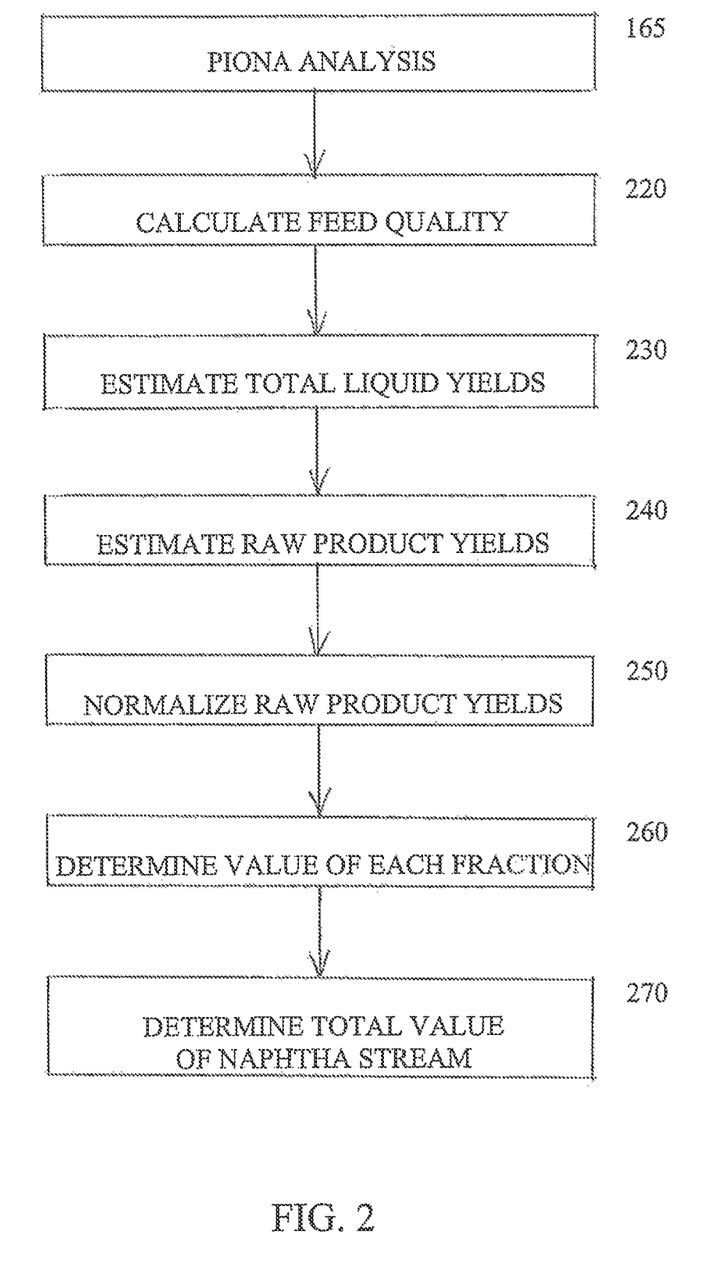
FIG. 2 is a process flow diagram of additional steps carried out to establish a value for naphtha streams using the system and method herein.

FIG. 2 shows a process flowchart of steps in a method according to one embodiment herein. Variable N is used to represent the total percentage of naphthenes by volume, and variable A is used to represent the total percentage of aromatics by volume, as derived from the PIONA analysis indicated at step 165 in FIG. 2.

In step 220, the feed quality is assigned as:

$$\text{Feed quality} = N + 2A \quad (1)$$

In step 230, the total liquid yield, Y, is assigned as a function of the feed quality and the constant RON number (i.e., the target number), Rt:

$$Y = KYa*(N+2A)^2 + KYb*(N+2A) + KYc*Rt^2 + KYd*Rt + KYe \quad (2)$$

where KYa through KYe are constants.

The individual yields for H2, C1, C2, C3, C4 and C5+ and the reformate yield can then be assigned. At step 240, the estimated raw product yields are assigned, for instance using equations (3)-(8), for methane, ethane, propane, butane and gasoline, using linear models based upon the total liquid products variable, while hydrogen is modeled linearly based upon the total liquid products variable and the constant RON number, Rt.

$$\text{Raw Methane Yield, } C1r = KC1ra*Y + KC1rb \quad (3)$$

$$\text{Raw Ethane Yield, } C2r = KC2ra*Y + KC2rb \quad (4)$$

$$\text{Raw Propane Yield, } C3r\ KC3ra*Y \pm KC3rb \quad (5)$$

$$\text{Raw Butane Yield, } C4r = KC4ra*Y + KC4rb \quad (6)$$

$$\text{Raw Gasoline Yield, } Gr = KGra*Y + KGrb \quad (7)$$

$$\text{Raw Hydrogen Yield, } Hr = KHra*Y + KHrb*Rt + KHrc \quad (8)$$

where KC1ra through KC4rb, KGra, KGrb, and KHRA through KHrc are constants.

The estimated total raw yield is the sum of the estimated raw yields for these components:

$$\text{Total Raw Yield, } Tr = C1r + C2r + C3r + C4r + Gr + Hr \quad (9)$$

In step 250, the yields are normalized to 100 by dividing the individual raw yields by the total raw yields, as follows:

$$\text{Normalized Methane Yield, } C1n = (C1r*100)/Tr \quad (10)$$

$$\text{Normalized Ethane Yield, } C2n = (C2r*100)/Tr \quad (11)$$

$$\text{Normalized Propane Yield, } C3n = (C3r*100)/Tr \quad (12)$$

$$\text{Normalized Butane Yield, } C4n = (C4r*100)/Tr \quad (13)$$

$$\text{Normalized Gasoline Yield, } Gn = (Gr*100)/Tr \quad (14)$$

$$\text{Normalized Hydrogen Yield, } Hn = (Hr*100)/Tr \quad (15)$$

In step 260, the estimated yield of each fraction is multiplied by its unit value, to assign a value to each fraction:

$$\text{Value of Methane, } C1v = (C1n/100)*C1P, \text{ where } C1P \text{ is methane's value} \quad (16)$$

$$\text{Value of Ethane, } C2v = (C2n/100)*C2P, \text{ where } C2P \text{ is ethane's value} \quad (17)$$

$$\text{Value of Propane, } C3v = (C3n/100)*C3P, \text{ where } C3P \text{ is propane's value} \quad (18)$$

$$\text{Value of Butane, } C4v = (C4n/100)*C4P, \text{ where } C4P \text{ is butane's value} \quad (19)$$

$$\text{Value of Gasoline, } Gv = (Gn/100)*GP, \text{ where } GP \text{ is gasoline's value} \quad (20)$$

$$\text{Value of Hydrogen, } Hv = (Hn/100)*HP, \text{ where } HP \text{ is hydrogen's value} \quad (21)$$

In step 270, the total value of the naphtha stream is then estimated by summing the calculated values of the individual streams:

$$\text{Naphtha Unit Value (\$/ton), } NPT = C1v + C2v + C3v + C4v + Gv + Hv \quad (22)$$

The value of the naphtha stream can also be restated as $/barrel, by dividing the value expressed as $/ton by the density and multiplying by the number of liters in a barrel of oil (159 liters/barrel):

$$NPB = (NPT/\text{Density})*159 \text{ liters/barrel} \quad (23)$$

When two naphtha streams are to be evaluated, this process can readily be used to assign values to each for comparison.

Figure 3:
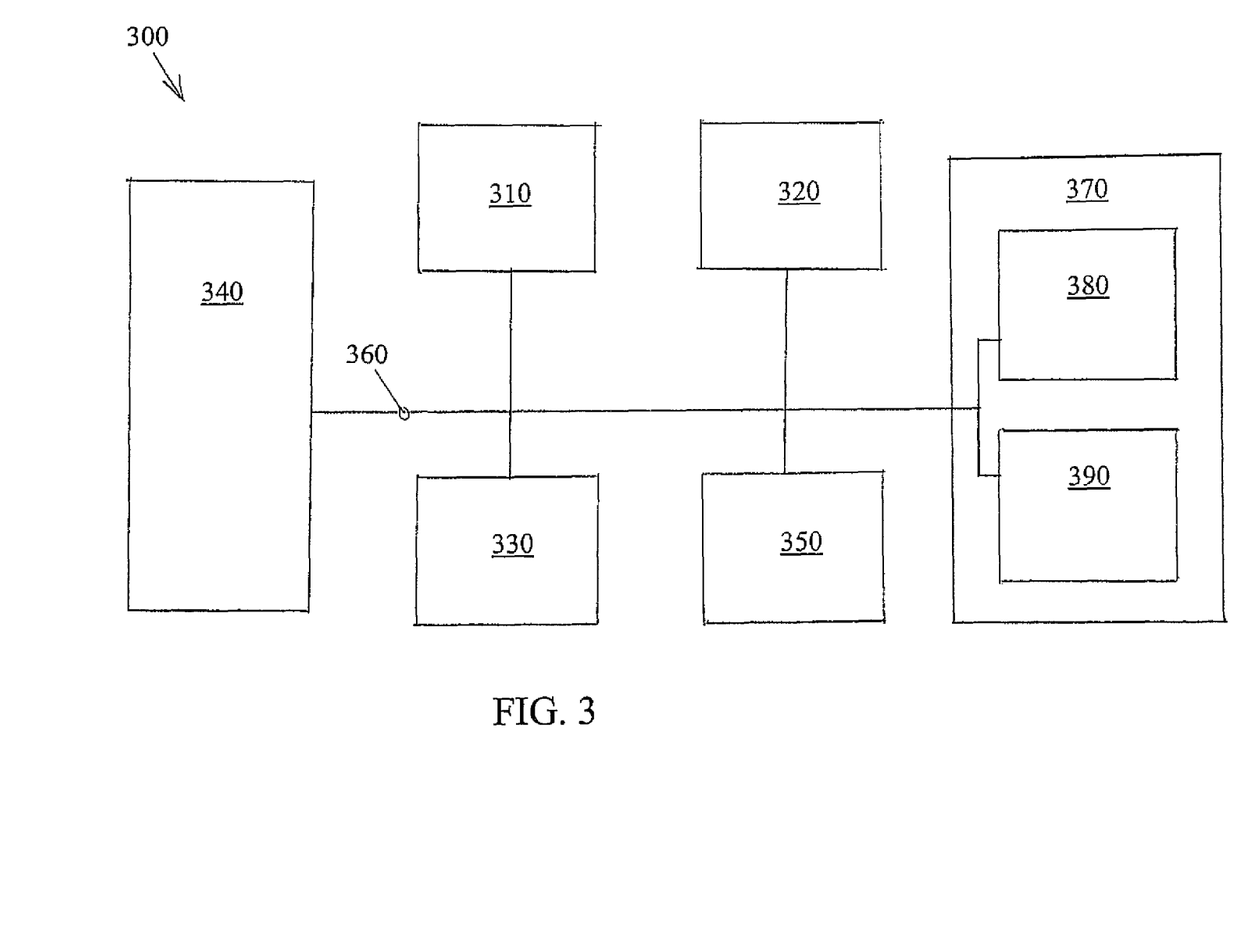
FIG. 3 is a block diagram of a component of a system for implementing the invention according to one embodiment.

An exemplary block diagram of a computer system 300 by which indicative property calculation modules operable, for instance, to carry out all or a portion of equations (1)-(23), can be implemented is shown in FIG. Computer system 300 includes a processor 310, such as a central processing unit, an input/output interface 320 and support circuitry 330. In certain embodiments, where the computer 300 requires direct human interaction, a display 340 and an input device 350 such as a keyboard, mouse or pointer are also provided. The display 340, input device 350, processor 310, input/output interface 320 and support circuitry 330 are shown connected to a bus 360 which also connects to a memory unit 370. Memory 370 includes program storage memory 380 and data storage memory 390. Note that while computer 300 is depicted with the direct human interface components of display 340 and input device 350, programming of modules and importation and exportation of data can also be accomplished over the interface 320, for instance, where the computer 300 is connected to a network and the programming and display operations occur on another associated computer, or via a detachable input device, as are well known in the art for interfacing programmable logic controllers.

Program storage memory 380 and data storage memory 390 can each comprise volatile (RAM) and non-volatile (ROM) memory units and can also comprise hard disk and backup storage capacity, and both program storage memory 380 and data storage memory 390 can be embodied in a single memory device or separated in plural memory devices. Program storage memory 380 stores software program modules and associated data, including one or more calculation modules such as a feed quality calculation module (e.g., corresponding to step 220 described above with respect to FIG. 2), yield calculation modules (e.g., corresponding to steps 230, 240 and 250 described above with respect to FIG. 2, including separate or individual modules for total reformer yield; total liquid yield; individual yields for H2, C1, C2, C3, C4 and C5+ and the reformate; total raw yield; and normalized yields), and valuation modules (e.g., corresponding to steps 260 and 270 described above with respect to FIG. 2). Data storage memory 390 stores data used and/or generated by the one or more modules of the present system, including PIONA analysis data or portions thereof used by the one or more modules of the present system, and calculated feed quality, yields and valuations generated by the one or more modules of the present system.

The calculated and assigned results in accordance with the systems and methods herein are displayed, audibly outputted, printed, and/or stored to memory for use as described herein.

It is to be appreciated that the computer system 300 can be any general or special purpose computer such as a personal computer, minicomputer, workstation, mainframe, a dedicated controller such as a programmable logic controller, or a combination thereof. While the computer system 300 is shown, for illustration purposes, as a single computer unit, the system can comprise a group/farm of computers which can be scaled depending on the processing load and database size, e.g., the total number of samples that are processed and results maintained on the system. The computer system 300 can serve as a common multi-tasking computer.

The computing device 300 preferably supports an operating system, for example, stored in program storage memory 390 and executed by the processor 310 from volatile memory. According to the present system and method, the operating system contains instructions for interfacing the device 300 to the calculation module(s).

Example

An exemplary PIONA analysis of a sample from a hydrotreated naphtha stream is shown in Table 1. Note that while most of the light components such as propane and butane present in the naphtha are separated, some light components will remain dissolved in the liquid reformate product, and thus will appear in the PIONA analysis.

TABLE 1

PIONA ANALYSIS OF A NAPHTHA STREAM
Hydrocarbon Family

| Carbon # | n-Paraffins | i-Paraffins | Naphthenes | Aromatics |
|---|---|---|---|---|
| C3 | 0.112% | 0% | 0% | 0% |
| C4 | 2.022% | 0.212% | 0% | 0% |
| C5 | 6.232% | 2.626% | 0.494% | 0% |
| C6 | 8.697% | 6.114% | 3.086% | 0.751% |
| C7 | 12.749% | 16.033% | 5.545% | 1.985% |
| C8 | 5.288% | 6.006% | 3.017% | 2.448% |
| C9 | 3.02% | 3.829% | 2.019% | 1.893% |
| C10 | 1.304% | 2.159% | 0.819% | 0.968% |

TABLE 1-continued

PIONA ANALYSIS OF A NAPHTHA STREAM
Hydrocarbon Family

| Carbon # | n-Paraffins | i-Paraffins | Naphthenes | Aromatics |
|---|---|---|---|---|
| C11 | 0.084% | 0.25% | 0.221% | 0.017% |
| Total* | 37.29% | 36.77% | 14.98% | 8.05% |

*Total = 97.09 V %, losses = 2.91 V %. (i.e., the yields are not normalized.)

Based on the data of Table 1, equations (1)-(23) can be used to assign the naptha value as a function of the feed quality and the target RON number, Rt. Thus, in the example given in Table 1, N=14.98, and A=8.05

$$\text{Feed quality}=N+2A=14.98+2*8.05=31.08 \qquad (1).$$

Equations and constants for assigning total reformer yield were developed from a linear regression of the N+2A concentration versus total yield. The individual yields for H2, C1, C2, C3, C4 and C5+ and the total reformate yield were calculated from a linear regression of the total reformate yield versus individual yields at the target research octane number. For these calculations, the following constants are applied:

$$KYa=-0.01702; KYb=2.192; KYc=-0.03333;$$
$$KYd=5.531; \text{ and } KYe=-206.63 \qquad \text{Eq. (2):}$$

$$KC1ra=-0.12393; KC1rb=11.42; KC2ra=-0.17991;$$
$$KC2rb=16.8; KC3ra=-0.25714;$$
$$KC3rb=24.24286; KC4ra=-018705;$$
$$KC4rb=27.27143; KGra=0.839255;$$
$$KGrb=18.09532; KHra=0.0605; KHrb=0.1; \text{ and}$$
$$KHrc=12.145. \qquad \text{Eqs. (3)-(8):}$$

Thus, for the example given in Table 1, when a target octane number for gasoline of 98 is selected, the yield equation (2) is as follows:

$$Y=KYa*(N+2A)^2+KYb*(N+2A)+KYc*Rt^2+KYd*Rt+KYe$$

$$(-0.01702)*(31.08)^2+2.192*31.08-0.03333*(98)^2+5.531*98-206.63$$

$$Y=66.99. \qquad (2)$$

The individual raw product yields are as follows:

$$C1r=KC1ra*Y+KC1rb=0.12393*66.99+11.42=3.11 \qquad (3)$$

$$C2r=KC2ra*Y+KC2rb=-0.17991*66.99+16.8=4.75 \qquad (4)$$

$$C3r=KC3ra*Y+KC3rb=-0.25714*66.99+24.24286=7.02 \qquad (5)$$

$$C4r=KC4ra*Y+KC4rb=-0.28705*66.99+27.27143=8.04 \qquad (6)$$

$$Gr=KGra*Y+KGrb=0.839255*66.99+18.09532=74.32 \qquad (7)$$

$$Hr=KHra*Y+KHrb*Rt+KHrc=0.0605*66.99+0.1*98-12.145=1.7 \qquad (8)$$

The Total Raw Yield is:

$$Tr = C1r + C2r + C3r + C4r + Gr + Hr \qquad (9)$$
$$= 3.11 + 4.75 + 7.02 + 8.04 + 74.32 + 1.71$$
$$= 98.95$$

The normalized product yields are as follows:

$$C1n = (C1r*100)/Tr = (3.11*100)/98.94917 = 3.14 \quad (10)$$

$$C2n = (C2r*100)/Tr = (4.75*100)/98.94917 = 4.80 \quad (11)$$

$$C3n = (C3r*100)/Tr = (7.02*100)/98.94917 = 7.09 \quad (12)$$

$$C4n = (C4r*100)/Tr = (8.04*100)/98.94917 = 8.13 \quad (13)$$

$$Gn = (Gr*100)/Tr = (74.32*100)/98.94917 = 75.11 \quad (14)$$

$$Hn = (Hr*100)/Tr(1.71*100)/98.94917 = 1.73 \quad (15)$$

Thus, if unit values are, for methane, C1P=$152.44/ton; for ethane, C2P=$149.81/ton; for propane, C3P=$343.71/ton; for butane, C4P=$499.03/ton; for gasoline, GP=$601.63/ton; and for hydrogen, HP=$391.60/ton, then the value of those products in the naphtha stream of Table 1 would be calculated as:

$$C1v = (3.14/100)*\$152.44/\text{ton} = \$4.80/\text{ton} \quad (16)$$

$$C2v = (4.80/100)*\$149.81/\text{ton} = \$7.19/\text{ton} \quad (17)$$

$$C3v = (7.09/100)*\$343.71/\text{ton} = \$24.37/\text{ton} \quad (18)$$

$$C4v = (8.13/100)*\$499.03/\text{ton} = \$40.57/\text{ton} \quad (19)$$

$$Gv = (75.11/100)*\$601.63/\text{ton} = \$451.88/\text{ton} \quad (20)$$

$$Hv = (1.73/100)*\$391.60/\text{ton} = \$6.77/\text{ton} \quad (21)$$

The value of the naphtha stream calculated by this method is:

$$NPT = 4.80 + 7.19 + 24.37 + 40.57 + 451.88 + 6.77 = \$535.58/\text{ton} \quad (22)$$

$$NPB = (\$535.58/\text{ton}/750 \text{ liters/ton})*159 \text{ liters/barrel} = \$113.54/\text{barrel} \quad (23)$$

In alternate embodiments, the present invention can be implemented as a computer program product for use with a computerized computing system. Those skilled in the art will readily appreciate that programs defining the functions of the present invention can be written in any appropriate programming language and delivered to a computer in any form, including but not limited to: (a) information permanently stored on non-writeable storage media (e.g., read-only memory devices such as ROMs or CD-ROM disks); (b) information alterably stored on writeable storage media (e.g., floppy disks and hard drives); and/or (c) information conveyed to a computer through communication media, such as a local area network, a telephone network, or a public network such as the Internet. When carrying computer readable instructions that implement the present invention methods, such computer readable media represent alternate embodiments of the present invention.

As generally illustrated herein, the system embodiments can incorporate a variety of computer readable media that comprise a computer usable medium having computer readable code means embodied therein. One skilled in the art will recognize that the software associated with the various processes described can be embodied in a wide variety of computer accessible media from which the software is loaded and activated. Pursuant to In re Beauregard, 35 USPQ2d 1383 (U.S. Pat. No. 5,710,578), the present invention contemplates and includes this type of computer readable media within the scope of the invention. In certain embodiments, pursuant to In re Nuijten, 500 F.3d 1346 (Fed. Cir. 2007) (U.S. patent application Ser. No. 09/211,928), the scope of the present claims is limited to computer readable media, wherein the media is both tangible and non-transitory.

The system and method of the present invention have been described above and with reference to the attached drawings; however, modifications will be apparent to those of ordinary skill in the art and the scope of protection for the invention is to be defined by the claims that follow.

I claim:

1. A system for assigning a value to a naphtha sample based upon naphthene and aromatic content of a reformate fraction of the naphtha sample at a target research octane number, the system comprising:
    a non-volatile memory device that stores calculation modules and data, the data including naphthene and aromatic content of the reformate fraction;
    a processor coupled to the memory;
    a first calculation module that calculates and assigns a total products yield as a function of the naphthene content, the aromatic content and the target research octane number;
    a second calculation module that calculates and assigns raw product yield to each of methane, ethane, propane, butane and gasoline as a function of the assigned total liquid products yield;
    a third calculation module that calculates and assigns a raw product yield of hydrogen as a function of the assigned total liquid product yield and the target research octane number; and
    a fourth calculation module that calculates and assigns values to each of hydrogen, methane, ethane, propane, butane and gasoline as a function of the raw product yields of each of hydrogen, methane, ethane, propane, butane and gasoline and a unit value of each product.

2. The system as in claim 1, further comprising a gas chromatograph that outputs data indicative of the naphthene and aromatic content of a reformate fraction of the naphtha sample at a target research octane number;
    wherein the data stored by the non-volatile memory device that stores calculation modules and data includes the outputted naphthene and aromatic content of the reformate fraction of the naphtha sample at the target research octane number.

3. A method for operating a computer to assign a value to a naphtha sample based upon naphthene and aromatic content of a reformate fraction of the naphtha sample at a target research octane number, the method comprising:
    entering into the computer data indicative of naphthene and aromatic content of the reformate fraction;
    calculating and assigning a total products yield as a function of the naphthene content, the aromatic content and the target research octane number;
    calculating and assigning a raw product yield to each of methane, ethane, propane, butane and gasoline as a function of the assigned total liquid products yield;
    calculating and assigning a raw product yield of hydrogen as a function of the assigned total liquid product yield and the target research octane number; and
    calculating and assigning a value to each of hydrogen, methane, ethane, propane, butane and gasoline as a function of the raw product yields of each of hydrogen, methane, ethane, propane, butane and gasoline and a unit value of each product.

4. The method as in claim 3, further comprising operating a gas chromatograph to obtain the data indicative of the naphthene and aromatic content of a reformate fraction of the naphtha sample at a target research octane number.

5. A system for determining the relative value of a stream of treated naphtha based upon a separately provided PIONA analysis of the fractions of the naphtha after processing in a reformer that is operated at a severity that yields a gasoline product having a predetermined constant research octane number, the system comprising:
- a memory that stores calculation modules and data, the data indicative of the content naphthenes and aromatics derived from the separately provided PIONA analysis of the fractions of the naphtha;
- a processor coupled to the memory;
- a calculation module that calculates and assigns the total liquid products yield as a function of the naphthene content, the aromatic content and the constant research octane number;
- a calculation module that calculates and assigns raw product yield to each of methane, ethane, propane, butane and gasoline as a function of the assigned total liquid products yield;
- a calculation module that calculates and assigns raw product yield of hydrogen as a function of the total liquid products yield and the constant research octane number (RON);
- a calculation module that calculates and assigns values to each of hydrogen, methane, ethane, propane, butane and gasoline as a function of the raw product yields of each of hydrogen, methane, ethane, propane, butane and gasoline, and a unit value of each product.

6. The system of claim 5 in which the treated naphtha stream contains less than 0.5 ppmw of sulfur and less than 0.5 ppmw nitrogen.

7. The system of claim 5 in which the RON is selected from the range of from 95 to 100.

8. The system of claim 7 in which the RON is selected from the range of from 95 to 98.

9. A method for operating a computer to determine the relative value of a treated naphtha stream derived from a crude oil sample obtained from a particular source, the method comprising:
- entering into the computer data indicative of the content naphthenes and aromatics derived from a separately provided PIONA analysis of the fractions of the naphtha stream that is processed in a reformer operated under conditions that produce a gasoline product having a predetermined constant research octane number;
- calculating and assigning the total liquid products yield as a function of the naphthene content, the aromatic content and the constant research octane number;
- calculating and assigning raw product yield to each of methane, ethane, propane, butane and gasoline as a function of the total liquid products yield;
- calculating and assigning raw product yield for hydrogen as a function of the total liquid products yield and the constant research octane number;
- calculating and assigning a to each of hydrogen, methane, ethane, propane, butane and gasoline as a function of the raw product yield to each of hydrogen, methane, ethane, propane, butane and gasoline, and a predetermined unit value for each product.

10. The method of claim 9 in which the treated naphtha stream contains less than 0.5 ppmw of sulfur and less than 0.5 ppmw of nitrogen.

11. The method of claim 9 in which the RON is selected from the range of from 95 to 100.

12. The method of claim 9 which includes the further steps of entering PIONA analyses from a plurality of samples derived from different crude oils and compiling the calculated estimated values for each of the treated naphthas to provide a listing of comparative values based upon a constant RON.

* * * * *